US009932596B2

(12) United States Patent
Lee et al.

(10) Patent No.: US 9,932,596 B2
(45) Date of Patent: Apr. 3, 2018

(54) RECOMBINANT MICROORGANISM PRODUCING 1,3-DIAMINOPROPANE AND METHOD FOR PRODUCING 1,3-DIAMINOPROPANE USING THE SAME

(71) Applicant: Korea Advanced Institute of Science and Technology, Daejeon (KR)

(72) Inventors: Sang Yup Lee, Daejeon (KR); Tong Un Chae, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/299,928

(22) Filed: Oct. 21, 2016

(65) Prior Publication Data

US 2017/0114345 A1    Apr. 27, 2017

(30) Foreign Application Priority Data

Oct. 22, 2015    (KR) .......................... 10-2015-0147590

(51) Int. Cl.
| | |
|---|---|
| C12P 13/00 | (2006.01) |
| C12N 1/16 | (2006.01) |
| C12N 1/20 | (2006.01) |
| C12N 15/52 | (2006.01) |
| C12N 9/10 | (2006.01) |
| C12N 9/88 | (2006.01) |

(52) U.S. Cl.
CPC .............. *C12N 15/52* (2013.01); *C12N 1/16* (2013.01); *C12N 1/20* (2013.01); *C12N 9/1096* (2013.01); *C12N 9/88* (2013.01); *C12P 13/001* (2013.01); *C12Y 206/01* (2013.01); *C12Y 401/01086* (2013.01)

(58) Field of Classification Search
None
See application file for complete search history.

(56) References Cited

U.S. PATENT DOCUMENTS

2013/0303723 A1    11/2013  Burk et al.

FOREIGN PATENT DOCUMENTS

WO    WO2016/153221 A1 *   9/2016   ............. C12N 15/63
                                                    435/320.1

OTHER PUBLICATIONS

GenBank Accession No. CP001172.1, published Nov. 21, 2011.*
GenBank Accession No. CP001182.1, published Nov. 21, 2011.*
(Continued)

*Primary Examiner* — Richard C Ekstrom
(74) *Attorney, Agent, or Firm* — Hultquist, PLLC; Steven J. Hultquist

(57) ABSTRACT

The present disclosure relates to a recombinant microorganism producing 1,3-diaminopropane, and a method for producing 1,3-diaminopropane using the same, and specifically, to a recombinant microorganism producing 1,3-diaminopropane into which genes encoding an enzyme involved in a metabolic pathway of 1,3-diaminopropane, dat and ddc, are introduced, and a method for producing 1,3-diaminopropane using the same.

When the recombinant microorganism producing the 1,3-diaminopropane according to the present disclosure is used, 1,3-diaminopropane may be mass-produced to be industrially useful in various fields such as pharmaceutical products, agricultural products, fibers for clothing, etc.

13 Claims, 5 Drawing Sheets

(56) References Cited

OTHER PUBLICATIONS

Lee et al., "Systems metabolic engineering of *Escherichia coli* for L-threonine production", Molecular Systems Biology 3:149, 2007.*

Machine English translation of Korean Application 10-2015-0039071, filed Mar. 20, 2015.*

Chae, T.U., et al., "Metabolic Engineering of *Escherichia coli* for the Production of 1,3-diaminopropane, a Three Carbon Diamine", "Scientific Reports", Aug. 11, 2015, pp. 1-13, vol. 5, No. 13040.

Chae, T.U., et al. (Kaist), "Metabolic Engineering of *Escherichia coli* for the Production of 1,3-diaminopropane, a Three Carbon Diamine", "KMB 2015 42nd Annual Meeting & International Symposium Jun. 24, 2015 ST3-2, 12:27-12:39", Jun. 24, 2015, p. 309.

Cui, X., et al., "Investigation on Odd-Odd Nylons Based on Undecanedioic Acid: 1. Synthesis and Characterization", "Polymer International", Jul. 30, 2004, pp. 1729-1734, vol. 53.

Cui, X., et al., "Synthesis and Characterization of Novel Even-Odd Nylons Based on Undecanedioic Acid", "European Polymer Journal", Jan. 31, 2004, pp. 1111-1118, vol. 40, Publisher: Elsevier Ltd.

Adams, M.D., et al., "Genbank Accession No. ACJ42229: diaminobutyrate--2-oxoglutarate aminotransferase [Acinetobacter baumannii AB0057]", Jan. 30, 2014, p. 1.

NCBI Reference Sequence: WP000227394.1, "Genbank Accession No. WP000227394: 2,4-diaminobutyrate decarboxylase [Acinetobacter baumannii]", May 14, 2013, p. 1.

Ikai, H., et al., "Identification and Analysis of a Gene Encoding L-2,4-Diaminobutyrate:2-Ketoglutarate 4-Aminotransferase Involved in the 1,3-Diaminopropane Production Pathway in Acinetobacter baumannii", "Journal of Bacteriology", Aug. 1997, pp. 5118-5125, vol. 179, No. 16.

Kind, S., et al., "From Zero to Hero—Production of Bio-Based Nylon from Renewable Resources Using Engineered Corynebacterium glutamicum", "Metabolic Engineering", May 14, 2014, pp. 113-123, vol. 25, Publisher: Elsevier Inc.

Mimitsuka, T., et al., "Metabolic Engineering of Corynebacterium glutamicum for Cadaverine Fermentation", "Bioscience, Biotechnology, and Biochemistry", Sep. 23, 2007, pp. 2130-2135, vol. 71, No. 9.

Neumann, E., et al., "Gene Transfer into Mouse Lyoma Cells by Electroporation in High Electric Fields", "The EMBO Journal", Jun. 30, 1982, pp. 841-845, vol. 1, No. 7.

Qian, Z., et al., "Metabolic Engineering of *Escherichia coli* for the Production of Putrescine: A Four Carbon Diamine", "Biotechnology and Bioengineering", Aug. 27, 2009, pp. 651-662, vol. 104, No. 4.

Qian, Z., et al., "Metabolic Engineering of *Escherichia coli* for the Production of Cadaverine: A Five Carbon Diamine", "Biotechnology and Bioengineering", Sep. 1, 2010, pp. 91-103. vol. 108.

Sambrook, J., et al., "Protocol II: Fresh Competent *E. coli* Prepared Using Calcium Chloride", "Molecular Cloning: A Laboratory Manual: Second Edition", 1989, pp. 1.81-1.84, Publisher: Cold Spring Harbor Laboratory Press, Published in: US.

Schneider, J., et al., "Improving Putrescine Production by Corynebacterium glutamicium by Fine-Tuning Ornithine Transcarbamolyase Activity Using a Plasmid Addiction System", "Applied Microbiology and Biotechnology", Feb. 28, 2012, pp. 169-178, vol. 95.

Tabor, C., et al., "Polyamines in Microorganisms", "Microbiological Reviews", Mar. 1985, pp. 81-99, vol. 49, No. 1.

Note: For the non-patent literature citations that no month of publication is indicated, the year of publication is more than 1 year prior to the effective filing date of the present application.

* cited by examiner

[FIG 1]
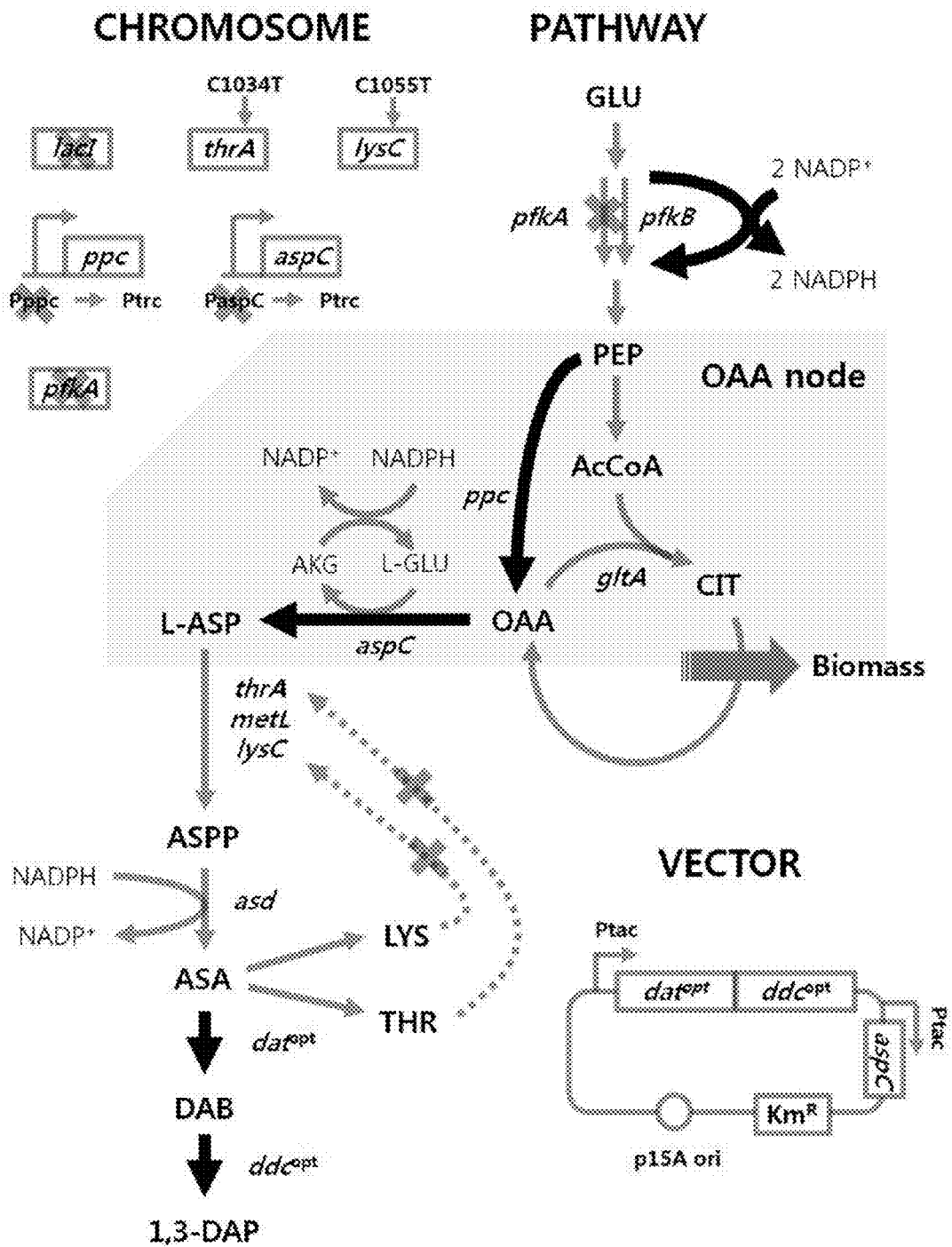

[FIG 2]
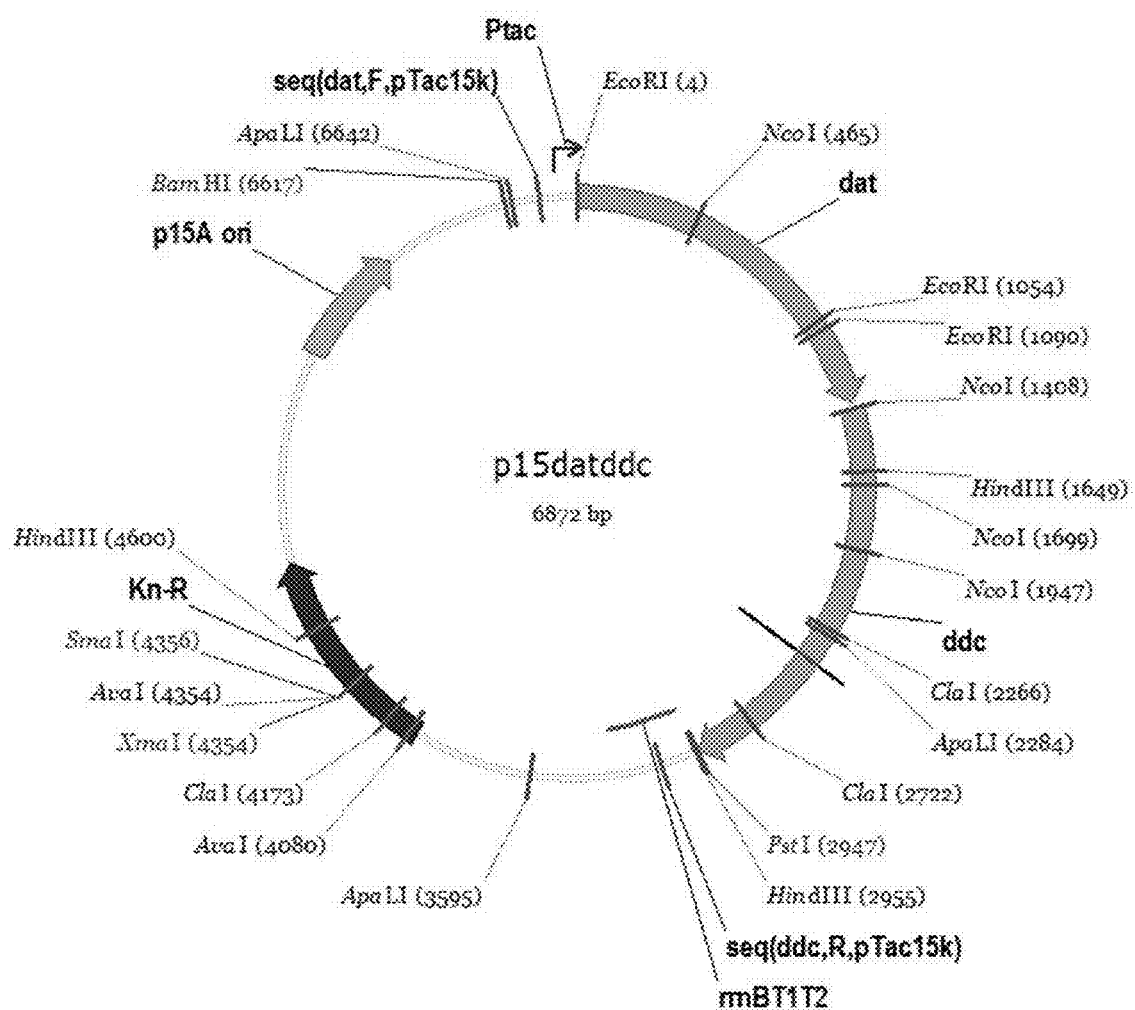

[FIG 3]
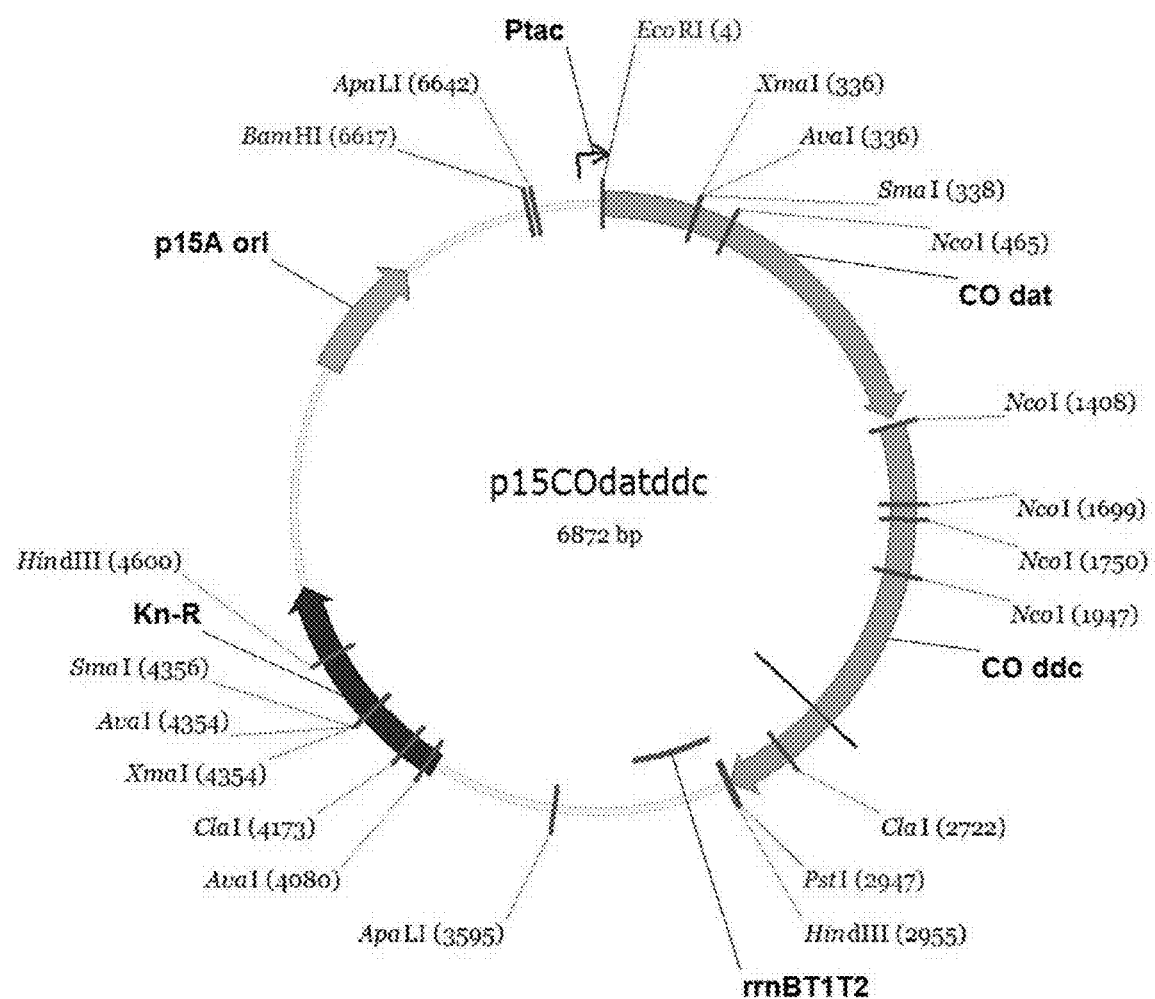

[FIG 4]
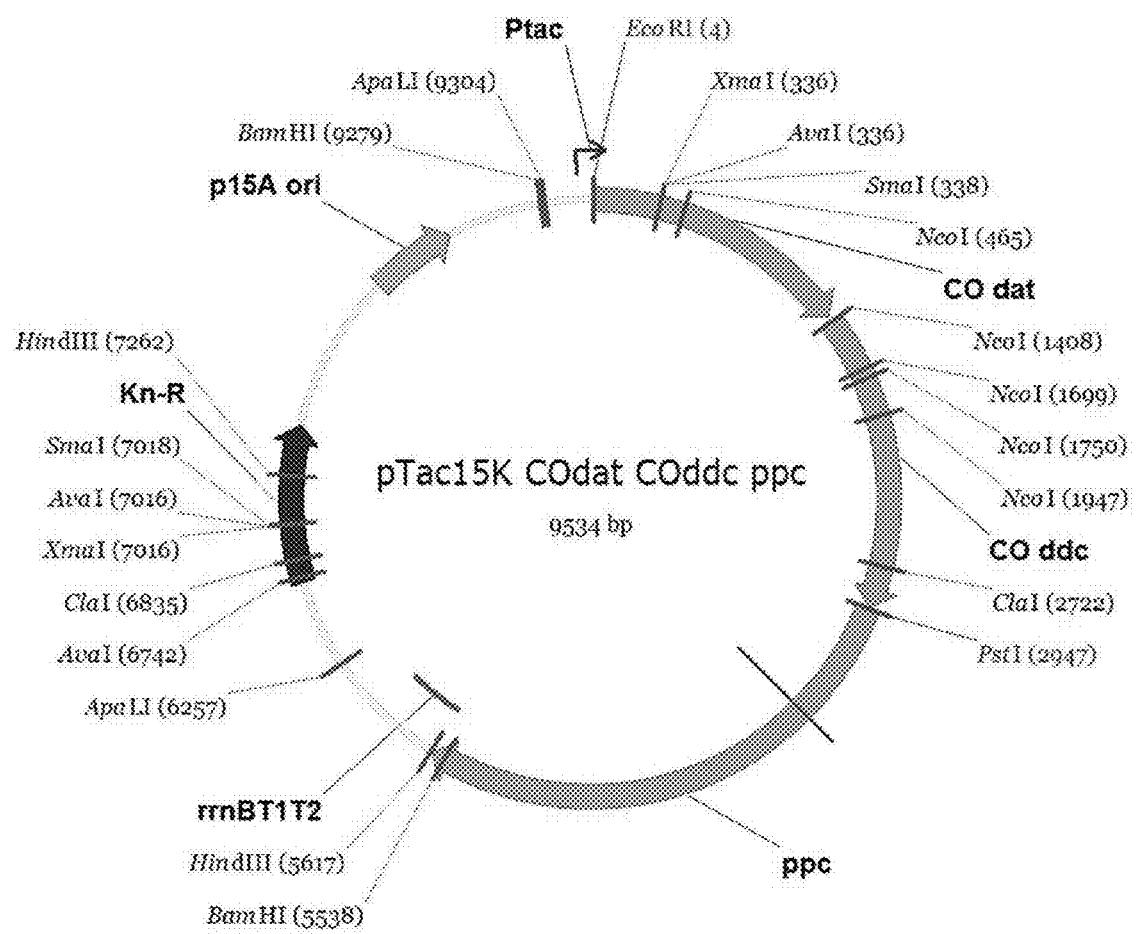

[FIG 5]
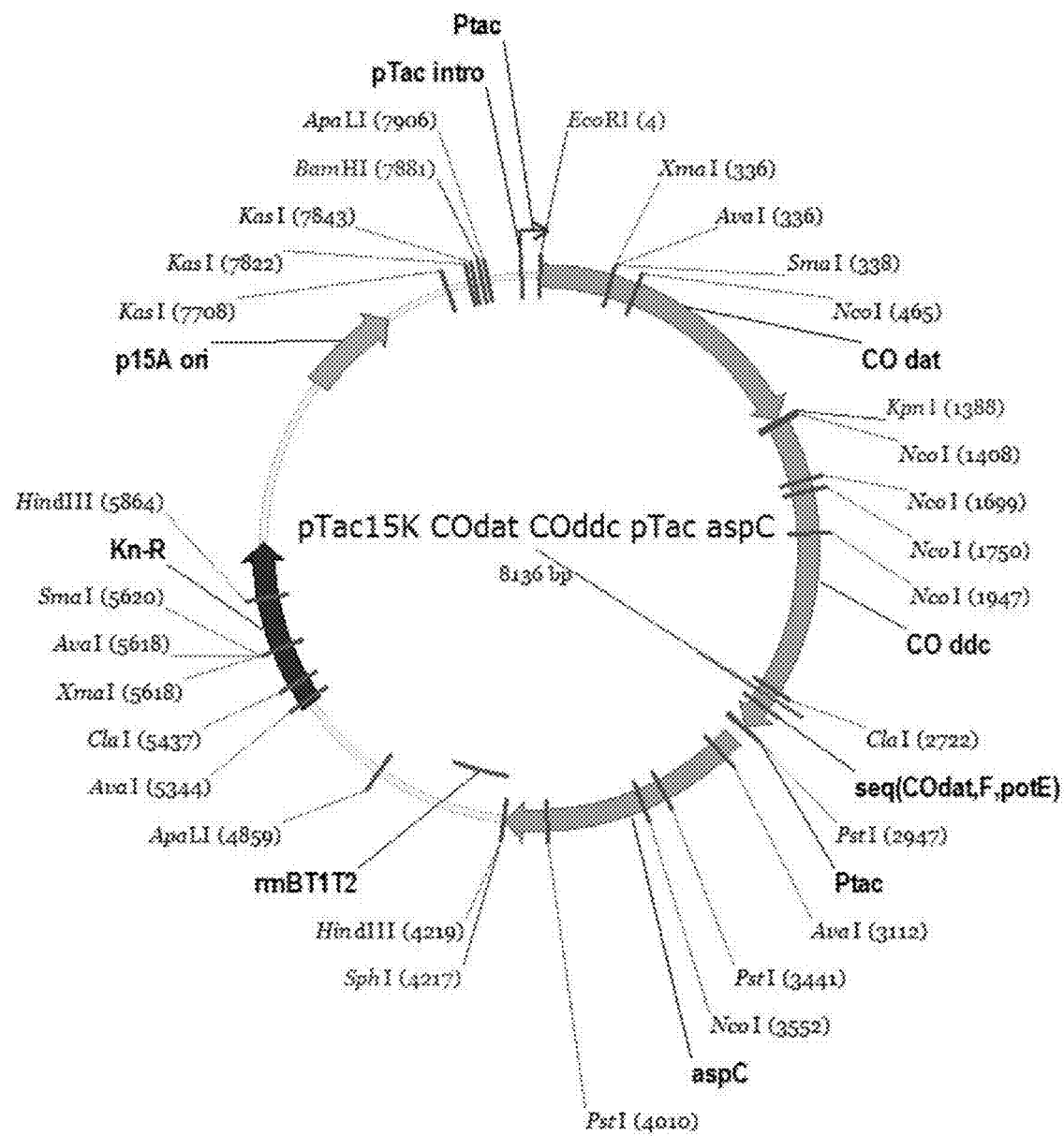

SEQUENCE LISTING

```
<160> NUMBER OF SEQ ID NOS: 21

<210> SEQ ID NO 1
<211> LENGTH: 457
<212> TYPE: PRT
<213> ORGANISM: Artificial Sequence
<220> FEATURE:
<223> OTHER INFORMATION: 2-ketoglutarate 4-aminotransferase amino acid
      sequence

<400> SEQUENCE: 1

Met Ser Val Thr Ser Val Asn Pro Ala Thr Asn Ala Thr Asn Glu Tyr
1               5                   10                  15

Tyr Leu Thr Arg Gln Ser Gln Met Glu Ser Asn Val Arg Ser Tyr Pro
            20                  25                  30

Arg Lys Leu Pro Leu Ala Ile Ala Lys Ala Gln Gly Cys Trp Val Thr
        35                  40                  45

Asp Val Glu Gly Thr Gln Tyr Leu Asp Cys Leu Ala Gly Ala Gly Thr
    50                  55                  60

Leu Ala Leu Gly His Asn His Pro Ala Val Ile Gln Ser Ile Gln Asp
65                  70                  75                  80

Thr Leu Ala Ser Gly Leu Pro Leu His Thr Leu Asp Leu Thr Thr Pro
                85                  90                  95

Leu Lys Asp Ala Phe Thr Glu Ala Leu Leu Ala Tyr Leu Pro Gly Gly
            100                 105                 110

Lys Glu Glu Tyr Cys Leu Gln Phe Cys Gly Pro Ser Gly Ala Asp Ala
        115                 120                 125

Thr Glu Ala Ala Ile Lys Leu Ala Lys Thr Tyr Thr Gly Arg Ser Ser
    130                 135                 140

Val Ile Ser Phe Ser Gly Gly Tyr His Gly Met Thr His Gly Ser Leu
145                 150                 155                 160

Ala Met Thr Gly Asn Leu Ser Ala Lys Asn Ala Val Asn Gly Leu Met
                165                 170                 175

Pro Gly Val Gln Phe Met Pro Tyr Pro His Glu Tyr Arg Cys Pro Leu
            180                 185                 190

Gly Leu Gly Gly Glu Ala Gly Val Asp Ala Leu Thr Tyr Tyr Phe Glu
        195                 200                 205

Asn Phe Ile Glu Asp Val Glu Ser Gly Val Thr Lys Pro Ala Ala Val
    210                 215                 220

Ile Leu Glu Ala Ile Gln Gly Glu Gly Gly Val Val Thr Ala Pro Val
225                 230                 235                 240

Lys Trp Leu Gln Lys Ile Arg Glu Val Thr Glu Lys His Asn Ile Val
                245                 250                 255
```

```
Leu Ile Leu Asp Glu Val Gln Ala Gly Phe Ala Arg Ser Gly Lys Met
        260                 265                 270

Phe Ala Phe Glu His Ala Ser Ile Glu Pro Asp Val Val Met Ser
        275                 280                 285

Lys Ala Val Gly Gly Leu Pro Leu Ala Val Leu Gly Ile Lys Arg
        290                 295                 300

Lys Phe Asp Ala Trp Gln Pro Ala Gly His Thr Gly Thr Phe Arg Gly
305                 310                 315                 320

Asn Gln Leu Ala Met Gly Thr Gly Leu Val Val Leu Glu Thr Ile Lys
                325                 330                 335

Glu Gln Asn Leu Ala Gln Asn Ala Glu Arg Gly Glu Phe Leu Gln
        340                 345                 350

Ala Glu Leu Lys Lys Leu Ala Thr Glu Phe Pro Cys Ile Gly Asn Val
        355                 360                 365

Arg Gly Arg Gly Leu Met Ile Gly Val Glu Ile Val Asp Glu Arg Lys
        370                 375                 380

Pro Ala Asp Arg Ile Gly Ser His Pro Ala Asp Ser Gln Leu Ala Ala
385                 390                 395                 400

Ala Ile Gln Thr Ala Cys Phe Asn Asn Lys Leu Leu Leu Glu Lys Gly
                405                 410                 415

Gly Arg Asn Gly Thr Val Ile Arg Leu Leu Cys Pro Leu Ile Ile Thr
                420                 425                 430

Gln Glu Glu Cys Val Glu Val Ile Ala Arg Phe Lys Lys Ala Val Ala
        435                 440                 445

Glu Ala Leu Val Ala Val Arg Gly Ala
        450                 455
```

<210> SEQ ID NO 2
<211> LENGTH: 510
<212> TYPE: PRT
<213> ORGANISM: Artificial Sequence
<220> FEATURE:
<223> OTHER INFORMATION: 2,4-diaminobutanoate decarboxylases amino acid
      sequence

<400> SEQUENCE: 2

```
Met Val Asp Phe Ala Glu His Arg Lys Ala Leu Leu Cys Asn Asp Ala
1               5                   10                  15

Gln Ser Ile Ala Asp Tyr Glu Ser Ala Met Gly Glu Ala Val Lys Ala
                20                  25                  30

Val Ser Ala Trp Leu Gln Asn Glu Lys Met Tyr Thr Gly Gly Ser Ile
        35                  40                  45

Lys Glu Leu Arg Ser Ala Ile Ser Phe Gln Pro Ser Lys Glu Gly Met
    50                  55                  60

Gly Val Gln Gln Ser Leu Gln Arg Met Ile Glu Leu Phe Leu Asn Lys
65                  70                  75                  80

Ser Leu Lys Val His His Pro His Ser Leu Ala His Leu His Cys Pro
                85                  90                  95

Thr Met Val Met Ser Gln Ile Ala Glu Val Leu Ile Asn Ala Thr Asn
                100                 105                 110

Gln Ser Met Asp Ser Trp Asp Gln Ser Pro Ala Gly Ser Leu Met Glu
        115                 120                 125

Val Gln Leu Ile Asp Trp Leu Arg Gln Lys Val Gly Tyr Gly Ser Gly
    130                 135                 140

Gln Ala Gly Val Phe Thr Ser Gly Gly Thr Gln Ser Asn Leu Met Gly
```

```
                145                 150                 155                 160
        Val Leu Leu Ala Arg Asp Trp Cys Ile Ser Lys Asn Trp Lys Asp Glu
                        165                 170                 175

Asn Gly Asn Pro Trp Ser Val Gln Arg Asp Gly Ile Pro Ala Glu Ala
                        180                 185                 190

Met Lys Asn Val Lys Val Ile Cys Ser Glu Asn Ala His Phe Ser Val
                        195                 200                 205

Gln Lys Asn Met Ala Met Met Gly Met Gly Phe Gln Ser Val Val Thr
                        210                 215                 220

Val Pro Val Asn Glu Asn Ala Gln Met Asp Val Asp Ala Leu Glu Lys
        225                 230                 235                 240

Thr Met Ala His Leu Gln Ala Glu Gly Lys Val Val Ala Cys Val Val
                        245                 250                 255

Ala Thr Ala Gly Thr Thr Asp Ala Gly Ala Ile Asp Pro Leu Lys Lys
                        260                 265                 270

Ile Arg Glu Ile Thr Asn Lys Tyr Gly Ser Trp Met His Ile Asp Ala
                        275                 280                 285

Ala Trp Gly Gly Ala Leu Ile Leu Ser Asn Asp Tyr Arg Ala Met Leu
                        290                 295                 300

Asp Gly Ile Glu Leu Ser Asp Ser Ile Thr Leu Asp Phe His Lys His
        305                 310                 315                 320

Tyr Phe Gln Ser Ile Ser Cys Gly Ala Phe Leu Leu Lys Asp Glu Ala
                        325                 330                 335

Asn Tyr Arg Phe Met His Tyr Glu Ala Glu Tyr Leu Asn Ser Ala Tyr
                        340                 345                 350

Asp Glu Glu His Gly Val Pro Asn Leu Val Ser Lys Ser Leu Gln Thr
                        355                 360                 365

Thr Arg Arg Phe Asp Ala Leu Lys Leu Trp Met Thr Ile Glu Ser Leu
                        370                 375                 380

Gly Glu Glu Leu Tyr Gly Ser Met Ile Asp His Gly Val Lys Leu Thr
        385                 390                 395                 400

Arg Glu Val Ala Asp Tyr Ile Lys Ala Thr Glu Gly Leu Glu Leu Leu
                        405                 410                 415

Val Glu Pro Gln Phe Ala Ser Val Leu Phe Arg Val Val Pro Glu Gly
                        420                 425                 430

Tyr Pro Val Glu Phe Ile Asp Ser Leu Asn Gln Asn Val Ala Asp Glu
                        435                 440                 445

Leu Phe Ala Arg Gly Glu Ala Asn Ile Gly Val Thr Lys Val Gly Asn
                        450                 455                 460

Val Gln Ser Leu Lys Met Thr Thr Leu Ser Pro Val Val Thr Val Asp
        465                 470                 475                 480

Asn Val Lys Asn Leu Leu Ala Gln Val Leu Ala Glu Ala Glu Arg Ile
                        485                 490                 495

Lys Asp Ala Ile Ala Ser Gly Asn Tyr Val Pro Pro Ile Asp
                        500                 505                 510

<210> SEQ ID NO 3
<211> LENGTH: 1374
<212> TYPE: DNA
<213> ORGANISM: Artificial Sequence
<220> FEATURE:
<223> OTHER INFORMATION: dat DNA sequence

<400> SEQUENCE: 3
atgagcgtta cttctgtcaa ccctgccact aatgctacca acgaatatta tttgactcgc      60
```

```
caaagtcaaa tggaatcgaa tgttcgtagc tatccacgta aattaccgtt agcgatagcg      120
aaagcacaag gttgctgggt tactgatgtt gaaggtacac agtaccttga ttgtttagct      180
ggggcaggta cattggcttt aggtcataat catcctgcgg tgattcaaag tattcaagac      240
acattggcaa gtggtttgcc attgcatact ttagacttaa ccacaccttt aaaagatgcg      300
tttactgaag cgttgttagc atatttacca ggtggtaaag aagaatattg cttacagttc      360
tgtggtcctt ctggtgcaga tgcgactgag gcagcaatta aacttgctaa aacttacact      420
ggccgtagct cagtgatcag tttctctggt ggttaccatg gtatgactca tggttcactt      480
gcaatgactg gtaacttaag tgcaaaaaat gcagtgaatg gcttaatgcc aggcgtacaa      540
ttcatgccat atccgcatga atatcgctgc ccacttggtt taggtggtga agctggtgtt      600
gacgctttaa cttactattt cgaaaacttt attgaagatg ttgaaagcgg tgtaactaag      660
cctgctgctg ttattcttga agcaattcaa ggtgaaggcg gtgttgttac agctccagta      720
aaatggttgc aaaaaatccg tgaagtgact gaaaagcaca acatcgtttt aattttagac      780
gaagttcaag caggctttgc tcgttcaggc aaaatgtttg catttgaaca tgccagtatt      840
gaacctgatg tcgttgtaat gtctaaagca gtaggtggtg gtttaccact tgcagtatta      900
ggtattaagc gtaaatttga tgcttggcag cctgctggcc acactggtac tttccgtggt      960
aaccaacttg ctatgggtac aggtcttgtt gtattagaaa cgatcaagga acaaaacctt     1020
gctcaaaatg cacaagagcg tggtgaattc ttacaagctg aattgaaaaa attagctact     1080
gaattcccat gtatcggtaa cgtacgtggc cgcggtttaa tgattggtgt tgaaatcgtt     1140
gacgagcgta aacctgctga ccgtatcggt tctcaccctg ctgactctca gttagcggct     1200
gcgatccaga ctgcttgctt taacaacaag ttattgcttg aaaaaggtgg tcgtaacggt     1260
acagtaattc gtttactttg cccactcatc attactcaag aagagtgtgt agaagtaatt     1320
gctcgcttta agaaagcagt tgcagaagca ttggttgcag tgcgaggcgc gtaa           1374
```

<210> SEQ ID NO 4  
<211> LENGTH: 1374  
<212> TYPE: DNA  
<213> ORGANISM: Artificial Sequence  
<220> FEATURE:  
<223> OTHER INFORMATION: datopt DNA sequence

<400> SEQUENCE: 4

```
atgtcggtta catctgtcaa cccggctact aatgctacca atgaatatta tttgacgcgc       60
cagagtcaaa tggaatcgaa tgtacgtagc tatccgagaa aattaccgct ggcgatagcg      120
aaagcccagg gctgctgggt tacagatgtg gaaggtacac agtaccttga ttgtttagcc      180
ggggcaggta cattggctct aggtcataat catccagcgg tgattcagag tatacaagac      240
accttggcct ccgggttgcc attacatacc ttagacttaa ccacccctct gaaggatgcg      300
tttacagagg cgctgttagc atatctcccg ggtggtaagg aggaatattg tctccagttc      360
tgtggcccct ctggtgccga tgcgactgaa gcagcaatta aacttgctaa aacttacacc      420
ggccgtagct cagtaatcag ttttctggt ggttaccatg gaatgacgca tggtagtctg      480
gcaatgactg gtaacctaag cgcaaaaaat gcagtgaacg gcctgatgcc cggcgtacaa      540
ttcatgccat atccgcatga atatcgctgc ccacttggat taggtggtga ggctggtgtg      600
gatgcgctca cttactattt tgagaatttt attgaagatg ttgaaagcgg agtaacgaag      660
ccggctgctg ttatttttaga agcaattcag ggtgaaggcg gtgttgttac agctcctgtc      720
```

```
aaatggttac agaagatccg tgaagtgact gaaaagcaca acatcgtgtt aattttagac    780
gaagttcaag cgggcttcgc ccgttcagga aaaatgtttg catttgaaca cgccgggatt    840
gaaccggatg tcgttgtgat gtcaaaagca gtcggaggtg gattaccact tgcagtatta    900
gggattaaaa ggaaatttga tgcttggcag cccgctggtc acaccggtac ttttcgtggc    960
aaccaacttg ctatgggaac aggtttagtt gtcttagaaa ccatcaagga acagaatctt   1020
gcgcaaaatg cccaggagcg tggagagttc ttacaggccg agttaaaaaa attagcgact   1080
gaatttccgt gtatcgggaa cgtccgtggc cgcggtctga tgataggagt ggaaatcgtt   1140
gacgagagaa aacctgccga ccggataggt tcccatcctg ccgattctca gttagcggct   1200
gccatccaaa ccgcgtgctt caataataaa ctgttgttag aaaaaggcgg tcgtaacggt   1260
acagtgattc gattactgtg cccccctcata attacgcagg aggagtgtgt agaagtgatt   1320
gcccgcttta agaaagcagt cgctgaagca ttggttgcag tgcggggcgc gtaa         1374
```

<210> SEQ ID NO 5
<211> LENGTH: 1533
<212> TYPE: DNA
<213> ORGANISM: Artificial Sequence
<220> FEATURE:
<223> OTHER INFORMATION: ddc DNA sequence

<400> SEQUENCE: 5

```
atggtggatt ttgcagaaca tcgtaaagcg ttactctgca atgatgcaca atccattgct     60
gactatgagt cagcaatggg cgaagcggta aaagccgttt cagcatggtt gcaaaatgaa    120
aaaatgtaca caggcggtag cattaaagag ttgcgttcag caatttcttt ccaaccttca    180
aaagaaggta tgggtgtaca acaatctctt caacgtatga ttgagctttt cttgaataaa    240
agcttgaaag tacaccatcc acattcatta gcacatttac actgcccaac catggtgatg    300
agccagatcg cggaagtgtt aatcaatgca actaaccagt ctatggactc atgggatcaa    360
agcccggcag gttcattaat ggaagtgcag cttattgatt ggttgcgtca aaaagtaggt    420
tacggttctg gtcaggcagg tgttttcact tctggcggta ctcaatctaa cttgatgggt    480
gtattacttg ctcgtgactg gtgtatctcg aaaaactgga agacgaaaaa tggtaaccca    540
tggtctgtac agcgtgatgg tattccagct gaagcaatga aaaacgtcaa agtcatttgt    600
tctgaaaatg cgcatttctc tgtgcaaaag aacatggcaa tgatgggcat gggcttccag    660
tcagttgtga ctgtacctgt gaatgaaaat gcacagatgg atgttgatgc tcttgaaaaa    720
acaatggcgc atcttcaagc tgaaggtaaa gttgttgctt gtgtcgttgc gacagcgggt    780
acaactgatg ctggtgcaat tgatccattg aaaaaaatcc gtgaaattac taataagtat    840
ggttcatgga tgcatatcga tgctgcgtgg ggcggtgcac tgatcttgtc aaatgactat    900
cgtgcaatgc ttgatggtat tgagctgtct gattcgatca ctctcgactt ccataagcat    960
tatttccaaa gcatcagctg tggtgcgttc ttgttaaaag atgaagcgaa ctatcgtttc   1020
atgcattatg aagctgagta cttgaactct gcttatgatg aagagcatgg cgtacctaac   1080
cttgtgtcta atcattaca acgactcgt cgttttgatg ctttaaaatt gtggatgacc   1140
attgaatcac tcggcgaaga gctatatggt tcaatgattg atcatggtgt aaaactgact   1200
cgtgaagttg cagattacat caaggcaact gaaggtttag agcttttagt tgaaccacaa   1260
tttgcttcgg tattgttccg tgttgttcca gaaggttacc cagttgagtt tatcgatagc   1320
ttgaaccaaa acgtagcaga tgaattgttt gcacgtggtg aagcaaatat tggtgtaaca   1380
aaagttggta atgtacagtc attgaagatg acaacattaa gccctgtagt aactgtcgac   1440
```

```
aacgttaaga acctttttagc tcaagtattg gctgaagctg aacgtattaa agatgcgatt    1500
gcttctggta actacgtacc accaatcgac taa                                 1533

<210> SEQ ID NO 6
<211> LENGTH: 1533
<212> TYPE: DNA
<213> ORGANISM: Artificial Sequence
<220> FEATURE:
<223> OTHER INFORMATION: ddcopt DNA sequence

<400> SEQUENCE: 6
atggtggatt ttgcagaaca tcgcaaggcg ctgctctgca atgatgcaca aagtattgct      60
gactatgaga gcgcaatggg cgaggcggtg aaagccgttt cagcgtggtt gcagaatgaa     120
aaaatgtaca ccggtgggtc gatcaaagag ttgcgctcag ccatttcttt ccagcctagc     180
aaggaaggta tgggggtcca gcaatccctt cagagaatga tagagctttt cctgaataag     240
agtctgaaag ttcaccatcc gcatagtctg gcccatttac actgcccaac catggtgatg     300
tcccagatcg cggaagtgtt aatcaatgca actaatcagt ccatggacag ttgggatcag     360
agcccggccg gtagcctgat ggaagtccag ttaattgatt ggttacgtca aaaagtaggt     420
tacggttcag ggcaagcagg tgtgtttacc tctggcggta cacagtctaa cttgatgggt     480
gtattgcttg cgcgggattg gtgcatagcg aaaaactgga agatgaaaa tggcaaccca     540 tggtctgtcc agagagacgg tattccagct gaagcaatga aaaacgtcaa agtcatttgt     600
tctgagaatg ctcactttag tgtgcaaaaa acatggcaa tgatgggcat gggctttcag     660
tcagttgtga ctgtacctgt gaacgaaaat gcccagatgg acgttgatgc ccttgagaaa     720
acgatggcgc atcttcaagc tgaaggtaag gttgttgcgt gtgttgttgc gacagcaggc     780
acaaccgatg ctggggccat tgatcctttg aaaaaaaatcc gggaaattac gaataaatat     840
ggtagctgga tgcatataga gctgcgtgg ggcggtgcat taatcttgtc gaatgactat     900
cgcgcaatgc tcgatggtat tgagttgtct gactcgatca ccctcgactt ccataagcat     960
tattttcaga gcattagctg tggcgcattc ttgttgaaag atgaagcgaa ttatcgtttt    1020
atgcactacg aagccgaata tttgaatagc gcttatgacg aagagcacgg tgtgcccaac    1080
cttgtgtcca agtcactcca gacgactagg cgttttgatg cattgaaact gtggatgacc    1140
atagaatcgc tcggcgaaga actatatggt tcaatgatta tcatggtgt gaaactgacg    1200 cgtgaagttg ccgattatat caaggccact gatgggttag agcttctagt tgagccgcaa    1260
tttgcttcgg tattgttccg tgttgttccg gaaggttacc cagttgagtt tatcgatagc    1320
ttgaaccaaa acgtagcgga tgaattgttc gcccgcggtg aggcaaatat tggggtcaca    1380
aaagttggca atgtccagtc attgaaaatg acaacgctga gccctgtagt aaccgtcgac    1440
aacgttaaga acctgttagc ccaggtcttg gctgaggctg aacgaattaa agatgcgatt    1500
gcttctggta attacgtgcc gcccatagac taa                                 1533

<210> SEQ ID NO 7
<211> LENGTH: 2652
<212> TYPE: DNA
<213> ORGANISM: Artificial Sequence
<220> FEATURE:
<223> OTHER INFORMATION: ppc DNA sequence

<400> SEQUENCE: 7
atgaacgaac aatattccgc attgcgtagt aatgtcagta tgctcggcaa agtgctggga      60
```

```
gaaaccatca aggatgcgtt gggagaacac attcttgaac gcgtagaaac tatccgtaag    120
ttgtcgaaat cttcacgcgc tggcaatgat gctaaccgcc aggagttgct caccacctta    180
caaaatttgt cgaacgacga gctgctgccc gttgcgcgtg cgtttagtca gttcctgaac    240
ctggccaaca ccgccgagca ataccacagc atttcgccga aggcgaagc tgccagcaac     300 ccggaagtga tcgcccgcac cctgcgtaaa ctgaaaaacc agccggaact gagcgaagac    360
accatcaaaa aagcagtgga atcgctgtcg ctggaactgg tcctcacggc tcacccaacc    420
gaaattaccc gtcgtacact gatccacaaa atggtggaag tgaacgcctg tttaaaacag    480
ctcgataaca aagatatcgc tgactacgaa cacaaccagc tgatgcgtcg cctgcgccag    540
ttgatcgccc agtcatggca taccgatgaa atccgtaagc tgcgtccaag cccggtagat    600
gaagccaaat ggggctttgc cgtagtggaa acagcctgt ggcaaggcgt accaaattac     660
ctgcgcgaac tgaacgaaca actggaagag aacctcggct acaaactgcc cgtcgaattt    720
gttccggtcc gttttacttc gtggatgggc ggcgaccgcg acggcaaccc gaacgtcact    780
gccgatatca cccgccacgt cctgctactc agccgctgga agccaccga tttgttcctg     840 aaagatattc aggtgctggt ttctgaactg tcgatggttg aagcgacccc tgaactgctg    900
gcgctggttg gcgaagaagg tgccgcagaa ccgtatcgct atctgatgaa aaacctgcgt    960
tctcgcctga tggcgacaca ggcatggctg gaagcgcgcc tgaaaggcga gaactgcca    1020 aaaccagaag gcctgctgac acaaaacgaa gaactgtggg aaccgctcta cgcttgctac    1080
cagtcacttc aggcgtgtgg catgggtatt atcgccaacg gcgatctgct cgacaccctg    1140
cgccgcgtga atgtttcgg cgtaccgctg gtccgtattg atatccgtca ggagagcacg    1200
cgtcataccg aagcgctggg cgagctgacc cgctacctcg gtatcggcga ctacgaaagc    1260
tggtcagagg ccgacaaaca ggcgttcctg atccgcgaac tgaactccaa cgtccgctt    1320 ctgccgcgca actggcaacc aagcgccgaa acgcgcgaag tgctcgatac ctgccaggtg    1380
attgccgaag caccgcaagg ctccattgcc gcctacgtga tctcgatggc gaaaacgccg    1440
tccgacgtac tggctgtcca cctgctgctg aaagaagcgg gtatcgggtt tgcgatgccg    1500
gttgctccgc tgtttgaaac cctcgatgat ctgaacaacg ccaacgatgt catgacccag    1560
ctgctcaata ttgactggta tcgtggcctg attcagggca aacagatggt gatgattggc    1620
tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg gcgagatgat ccgctttaaa    1860
tatggtctgc cagaaatcac cgtcagcagc ctgtcgcttt ataccggggc gattctggaa    1920
gccaacctgc tgccaccgcc ggagccgaaa gagagctggc gtcgcattat ggatgaactg    1980
tcagtcatct cctgcgatgt ctaccgcggc tacgtacgtg aaaacaaaga tttttgtgcct    2040 tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acggcaaaca gagcgagctg gaggctatgt gccgcgattg ccattcttc    2280 tcgacgcgtc tcggcatgct ggagatggtc ttcgccaaag cagacctgtg gctggcggaa    2340
tactatgacc aacgcctggt agacaaagca ctgtggccgt aggtaaaga gttacgcaac    2400 ctgcaagaag aagacatcaa agtggtgctg gcgattgcca acgattccca tctgatggcc    2460
```

| | | |
|---|---|---|
| gatctgccgt ggattgcaga gtctattcag ctacggaata tttacaccga cccgctgaac | 2520 | |
| gtattgcagg ccgagttgct gcaccgctcc cgccaggcag aaaaagaagg ccaggaaccg | 2580 | |
| gatcctcgcg tcgaacaagc gttaatggtc actattgccg ggattgcggc aggtatgcgt | 2640 | |
| aataccggct aa | 2652 | |

<210> SEQ ID NO 8
<211> LENGTH: 1191
<212> TYPE: DNA
<213> ORGANISM: Artificial Sequence
<220> FEATURE:
<223> OTHER INFORMATION: aspC DNA sequence
<400> SEQUENCE: 8

| | |
|---|---|
| atgtttgaga acattaccgc cgctcctgcc gacccgattc tgggcctggc cgatctgttt | 60 |
| cgtgccgatg aacgtcccgg caaaattaac ctcgggattg gtgtctataa agatgagacg | 120 |
| ggcaaaaccc cggtactgac cagcgtgaaa aaggctgaac agtatctgct cgaaaatgaa | 180 |
| accaccaaaa attacctcgg cattgacggc atccctgaat ttggtcgctg cactcaggaa | 240 |
| ctgctgtttg gtaaaggtag cgccctgatc aatgacaaac gtgctcgcac ggcacagact | 300 |
| ccgggggggca ctggcgcact acgcgtggct gccgatttcc tggcaaaaaa taccagcgtt | 360 |
| aagcgtgtgt gggtgagcaa cccaagctgg ccgaaccata gagcgtcttt aactctgca | 420 |
| ggtctggaag ttcgtgaata cgcttattat gatgcggaaa atcacactct tgacttcgat | 480 |
| gcactgatta acagcctgaa tgaagctcag gctggcacg tagtgctgtt ccatggctgc | 540 |
| tgccataacc caaccggtat cgaccctacg ctggaacaat ggcaaacact ggcacaactc | 600 |
| tccgttgaga aaggctggtt accgctgttt gacttcgctt accagggttt tgcccgtggt | 660 |
| ctggaagaag atgctgaagg actgcgcgct ttcgcggcta tgcataaaga gctgattgtt | 720 |
| gccagttcct actctaaaaa ctttggcctg tacaacgagc gtgttggcgc ttgtactctg | 780 |
| gttgctgccg acagtgaaac cgttgatcgc gcattcagcc aaatgaaagc ggcgattcgc | 840 |
| gctaactact ctaacccacc agcacacggc gcttctgttg ttgccaccat cctgagcaac | 900 |
| gatgcgttac gtgcgatttg ggaacaagag ctgactgata tgcgcagcg tattcagcgt | 960 |
| atgcgtcagt tgttcgtcaa tacgctgcag gaaaaaggcg caaaccgcga cttcagcttt | 1020 |
| atcatcaaac agaacggcat gttctccttc agtggcctga caaaagaaca agtgctgcgt | 1080 |
| ctgcgcgaag agtttggcgt atatgcggtt gcttctggtc gcgtaaatgt ggccgggatg | 1140 |
| acaccagata acatggctcc gctgtgcgaa gcgattgtgg cagtgctgta a | 1191 |

<210> SEQ ID NO 9
<211> LENGTH: 35
<212> TYPE: DNA
<213> ORGANISM: Artificial Sequence
<220> FEATURE:
<223> OTHER INFORMATION: p1

<400> SEQUENCE: 9

| | |
|---|---|
| agacaggaat tcatgtcggt tacatctgtc aaccc | 35 |

<210> SEQ ID NO 10
<211> LENGTH: 28
<212> TYPE: DNA
<213> ORGANISM: Artificial Sequence
<220> FEATURE:
<223> OTHER INFORMATION: p2

```
<400> SEQUENCE: 10
agacagggta ccttacgcgc cccgcact                                          28

<210> SEQ ID NO 11
<211> LENGTH: 54
<212> TYPE: DNA
<213> ORGANISM: Artificial Sequence
<220> FEATURE:
<223> OTHER INFORMATION: p3

<400> SEQUENCE: 11
agacagggta cctttcacac aggaaacaga ccatggtgga ttttgcagaa catc            54

<210> SEQ ID NO 12
<211> LENGTH: 32
<212> TYPE: DNA
<213> ORGANISM: Artificial Sequence
<220> FEATURE:
<223> OTHER INFORMATION: p4

<400> SEQUENCE: 12
agacagctgc agttagtcta tgggcggcac gt                                    32

<210> SEQ ID NO 13
<211> LENGTH: 73
<212> TYPE: DNA
<213> ORGANISM: Artificial Sequence
<220> FEATURE:
<223> OTHER INFORMATION: p5

<400> SEQUENCE: 13
tgcttctggt aattacgtgc cgcccataga ctaactgcag acaggaaaca atgaacgaac      60
aatattccgc att                                                        73

<210> SEQ ID NO 14
<211> LENGTH: 63
<212> TYPE: DNA
<213> ORGANISM: Artificial Sequence
<220> FEATURE:
<223> OTHER INFORMATION: p6

<400> SEQUENCE: 14
aaatcttctc tcatccgcca aaacagccaa gcttgcatgc ttagccggta ttacgcatac      60
ctg                                                                   63

<210> SEQ ID NO 15
<211> LENGTH: 20
<212> TYPE: DNA
<213> ORGANISM: Artificial Sequence
<220> FEATURE:
<223> OTHER INFORMATION: p7

<400> SEQUENCE: 15
gcatgcaagc ttggctgttt                                                 20

<210> SEQ ID NO 16
<211> LENGTH: 21
<212> TYPE: DNA
<213> ORGANISM: Artificial Sequence
<220> FEATURE:
<223> OTHER INFORMATION: p8

<400> SEQUENCE: 16
ctgcagttag tctatgggcg g                                               21
```

<210> SEQ ID NO 17
<211> LENGTH: 72
<212> TYPE: DNA
<213> ORGANISM: Artificial Sequence
<220> FEATURE:
<223> OTHER INFORMATION: p9

<400> SEQUENCE: 17

```
tgcttctggt aattacgtgc cgcccataga ctaactgcag acaggaaaca atgtttgaga      60
acattaccgc cg                                                         72
```

<210> SEQ ID NO 18
<211> LENGTH: 60
<212> TYPE: DNA
<213> ORGANISM: Artificial Sequence
<220> FEATURE:
<223> OTHER INFORMATION: p10

<400> SEQUENCE: 18

```
aaatcttctc tcatccgcca aaacagccaa gcttgcatgc ttacagcact gccacaatcg      60
```

<210> SEQ ID NO 19
<211> LENGTH: 63
<212> TYPE: DNA
<213> ORGANISM: Artificial Sequence
<220> FEATURE:
<223> OTHER INFORMATION: p11

<400> SEQUENCE: 19

```
tgcttctggt aattacgtgc cgcccataga ctaactgcag gctgttgaca attaatcatc      60
ggc                                                                   63
```

<210> SEQ ID NO 20
<211> LENGTH: 63
<212> TYPE: DNA
<213> ORGANISM: Artificial Sequence
<220> FEATURE:
<223> OTHER INFORMATION: p12

<400> SEQUENCE: 20

```
ggcaggagcg gcggtaatgt tctcaaacat tgtttcctgt gtgaaattgt tatccgctca      60
caa                                                                   63
```

<210> SEQ ID NO 21
<211> LENGTH: 27
<212> TYPE: DNA
<213> ORGANISM: Artificial Sequence
<220> FEATURE:
<223> OTHER INFORMATION: p13

<400> SEQUENCE: 21

```
acaggaaaca atgtttgaga acattac                                         27
```

RECOMBINANT MICROORGANISM PRODUCING 1,3-DIAMINOPROPANE AND METHOD FOR PRODUCING 1,3-DIAMINOPROPANE USING THE SAME

CROSS-REFERENCE TO RELATED APPLICATIONS

This application claims priority under 35 U.S.C. §119 of Korean Patent Application No. 10-2015-0147590 filed Oct. 22, 2015. The disclosure of such Korean priority patent application is hereby incorporated herein by reference in its entirety, for all purposes.

TECHNICAL FIELD

The present disclosure relates to a recombinant microorganism producing 1,3-diaminopropane, and a method for producing 1,3-diaminopropane using the same, and specifically, to a recombinant microorganism producing 1,3-diaminopropane into which genes encoding an enzyme involved in a metabolic pathway of 1,3-diaminopropane, dat and ddc, are introduced, and a method for producing 1,3-diaminopropane using the same.

BACKGROUND ART

In recent years, there is growing concern about depletion and environmental problems of limited oil resources due to an increase in unstable oil prices and a rapid change in climate. In order to solve this concern, there is an increase in demand for a variety of alternative techniques for breaking petrochemical-based chemical industry, and researches have been focused on obtaining various value-added compounds from microorganisms. Among the researches, a number of researches into production of diamine that is a nylon precursor and commercialization thereof are in progress.

Putrescine that is a diamine having four carbon lengths (Qian et al., *Biotechnol. Bioeng.* 104:651-662, 2009; Schneider et al., *Appl. Microbiol. Biotechnol.* 95:169-178, 2012) and cadaverine that is a diamine having five carbon lengths (Qian et al., *Biotechnol. Bioeng.* 108:93-103, 2011; Mimitsuka et al., *Biosci. Biotech. Bioch.* 71:3295-2135, 2007; Kind et al., *Metab. Eng.* 25:113-123, 2014) were produced by using the microorganism until now. Further, even though it has not been reported to produce 1,6-diaminohexane that is a diamine having 6 carbon lengths, there is a patent in which metabolic pathways capable of producing 1,6-diaminohexane have been designed (US 2013/0303723 A1). As described above, the researches into production of diamines having several carbon lengths using the microorganisms and commercialization thereof are in progress, but it has not been reported to produce 1,3-diaminopropane that is a diamine having 3 carbon lengths in the microorganism until the present.

1,3-diaminopropane (1,3-DAP) is an industrially important chemical, and is widely used as a crosslinking agent for an epoxy resin, and is used as precursors of various pharmaceutical products, agricultural products and organic compounds. In particular, various nylons are able to be produced by polymerizing the 1,3-diaminopropane (1,3-DAP) with dicarboxylic acid (Cui et al., *Polymer International* 53:1729-1734, 2004; Cui et al., *European polymer journal* 40:1111-1118, 2004). The 1,3-diaminopropane is produced by a very small number of microorganisms (Tabor et al., *Microbiol. Rev.* 49:81-99, 1985), and *Acinetobacter* species bio-synthesizes the 1,3-diaminopropane using 2-ketoglutarate 4-aminotransferase (dat) that is an enzyme converting aspartate-4-semialdehyde (ASA) into 2,4-diaminobutanoate (DAB), and 2,4-diaminobutanoate decarboxylase (ddc) that is an enzyme converting 2,4-diaminobutanoate (DAB) into 1,3-diaminopropane. However, there is no report on detection of 1,3-diaminopropane in a medium outside the microorganism yet.

Therefore, the present inventors made an effort to develop a recombinant microorganism capable of producing 1,3-diaminopropane, and as a result, found that the recombinant microorganism expressing 2-ketoglutarate 4-aminotransferase and 2,4-diaminobutanoate decarboxylase derived from *Acinetobacter baumannii* could produce the 1,3-diaminopropane, and completed the present disclosure.

DISCLOSURE

Technical Problem

An object of the present disclosure is to provide a recombinant microorganism producing 1,3-diaminopropane, and a method for producing the recombinant microorganism.

Another object of the present disclosure is to provide a method for producing 1,3-diaminopropane using the recombinant microorganism.

Technical Solution

In order to achieve the foregoing objects, the present disclosure provides a recombinant microorganism producing 1,3-diaminopropane in which a gene encoding 2-ketoglutarate 4-aminotransferase (dat) and a gene encoding 2,4-diaminobutanoate decarboxylase (ddc) are introduced into a microorganism having an ability of producing aspartate-4-semialdehyde (ASA).

The present disclosure also provides a method for producing a recombinant microorganism producing 1,3-diaminopropane including introducing a gene encoding 2-ketoglutarate 4-aminotransferase (dat) and a gene encoding 2,4-diaminobutanoate decarboxylase (ddc) into a microorganism having an ability of producing aspartate-4-semialdehyde (ASA).

The present disclosure further provides a method for producing 1,3-diaminopropane including: (a) producing 1,3-diaminopropane by culturing the recombinant microorganism; and (b) recovering the produced 1,3-diaminopropane.

DESCRIPTION OF DRAWINGS

FIG. 1 is a schematic diagram showing a 1,3-diaminopropane biosynthesis pathway.

FIG. 2 shows a p15DD plasmid in which dat and ddc genes are inserted.

FIG. 3 shows a p15DD$^{opt}$ plasmid in which codon optimized dat$^{opt}$ and dde$^{opt}$ genes are inserted.

FIG. 4 shows a p15DD$^{opt}$ppc plasmid in which codon optimized dat$^{opt}$ and dde$^{opt}$ genes, and ppc gene are inserted.

FIG. 5 shows a p15DD$^{opt}$paspC plasmid in which codon optimized dat$^{opt}$ and dde$^{opt}$ genes, a tac promoter, and an aspC gene are inserted.

BEST MODE

In the present disclosure, a recombinant microorganism for producing 1,3-diaminopropane was produced by introducing a gene encoding an enzyme involved in a metabolic pathway of 1,3-diaminopropane into a microorganism that does not produce the 1,3-diaminopropane to express the gene, and it was confirmed that the 1,3-diaminopropane was produced by using the same.

The metabolic pathway of 1,3-diaminopropane of the present disclosure consists of 2-ketoglutarate 4-aminotransferase and 2,4-diaminobutanoate decarboxylase. The 2-ketoglutarate 4-aminotransferase is an enzyme converting aspartate-4-semialdehyde into 2,4-diaminobutanoate, and the 2,4-diaminobutanoate decarboxylase is an enzyme converting 2,4-diaminobutanoate into 1,3-diaminopropane.

In an aspect of the present disclosure, the present disclosure relates to a recombinant microorganism producing 1,3-diaminopropane in which a gene encoding 2-ketoglutarate 4-aminotransferase (dat) and a gene encoding 2,4-diaminobutanoate decarboxylase (ddc) are introduced into a microorganism having an ability of producing aspartate-4-semialdehyde (ASA).

In the present disclosure, the microorganism may be exemplified by *Escherichia* genus, *Bacillus* genus, *Corynebacterium* genus, *Pichia* genus, *Pseudomonas* genus, *Saccharomyces* genus, etc., preferably, may be *Escherichia* genus microorganism, and the most preferably, *E. coli*. In particular, the *E. coli* is an industrially and largely used strain, and has an advantage of being easily industrialized since genetic information and culture condition are known.

In an exemplary embodiment of the present disclosure, in order to produce the microorganism producing 1,3-diaminopropane, a recombinant plasmid p15D was constructed by inserting a fragment of dat which is a gene encoding 2-ketoglutarate 4-aminotransferase derived from *Acinetobacter baumannii* in a pTac15k plasmid performing strong gene expression with a tac promoter, and then, a fragment of ddc which is a gene encoding 2,4-diaminobutanoate decarboxylase derived from *Acinetobacter baumannii* was inserted in the p15D to construct a recombinant plasmid p15DD.

In another exemplary embodiment of the present disclosure, in order to improve production capacity of 1,3-diaminopropane in *E. coli*, a recombinant plasmid p15D$^{opt}$ was constructed by inserting a fragment of dat$^{opt}$ which is a gene encoding 2-ketoglutarate 4-aminotransferase optimized in codon of the *E. coli* in the pTac15k plasmid performing strong gene expression with the tac promoter, and then, a fragment of dde$^{opt}$ which is a gene encoding 2,4-diaminobutanoate decarboxylase optimized in codon of the *E. coli* was inserted in the p15D$^{opt}$ to construct a recombinant plasmid p15DD$^{opt}$.

In still another exemplary embodiment of the present disclosure, in order to improve production capacity of the 1,3-diaminopropane by removing feedback inhibiting production of 1,3-diaminopropane in *E. coli*, a recombinant microorganism in which C of 1034$^{th}$ base sequence of a gene encoding aspartokinase I is substituted with T, or C of 1055$^{th}$ base sequence of a gene encoding aspartokinase III is substituted with T, was produced. Further, in order to improve the production capacity of the 1,3-diaminopropane by increasing pool of oxaloacetate (OAA) or aspartate (L-ASP) in the recombinant microorganism, a recombinant microorganism in which ppc which is a gene encoding phosphoenolpyruvate carboxylase and/or aspC which is a gene encoding aspartate aminotransferase, was over-expressed with a strong promoter, trc or tac, was produced. In addition, in order to improve production capacity of the 1,3-diaminopropane by increasing pool of NADPH, a recombinant microorganism in which a gene (pfkA) encoding 6-phosphofructokinase I was further deleted from the above recombinant microorganism, was produced.

In the present disclosure, the microorganism producing the 1,3-diaminopropane may comprise further variation selected from the group consisting of (i) mutation of base sequence of a gene encoding aspartokinase I and/or a gene encoding aspartokinase III to remove feedback inhibiting production of 1,3-diaminopropane; (ii) over-expression of a gene encoding phosphoenolpyruvate carboxylase and/or a gene encoding aspartate aminotransferase; and (iii) deletion of a gene encoding 6-phosphofructokinase I, wherein it is preferred that the mutation of the base sequence of the gene encoding the aspartokinase I includes substitution of 1034$^{th}$ base sequence C with T, or the mutation of the base sequence of the gene encoding the aspartokinase III includes substitution of 1055$^{th}$ base sequence C with T, but the mutation is not limited thereto.

In the present disclosure, the over-expression may comprise substitution of a promoter of the gene encoding phosphoenolpyruvate carboxylase and/or the gene encoding aspartate aminotransferase with a strong promoter or may comprise introduction of an expression vector containing the gene encoding phosphoenolpyruvate carboxylase and/or the gene encoding aspartate aminotransferase, and the strong promoter, but the over-expression is not limited thereto.

In the present disclosure, the strong promoter may be selected from the group consisting of a trc promoter, a tac promoter, a T7 promoter, a lac promoter, and a trp promoter.

In the present disclosure, the gene encoding the 2-ketoglutarate 4-aminotransferase (dat) and the gene encoding 2,4-diaminobutanoate decarboxylase (ddc) are preferably derived from the *Acinetobacter baumannii*, but the present disclosure is not limited thereto. Specifically, even though the gene is derived from various different microorganisms encoding the enzyme involved in the metabolic pathway of 1,3-diaminopropane, the gene is not limited as long as it is introduced into a host microorganism and expressed to have the same enzyme activity.

In the present disclosure, the 2-ketoglutarate 4-aminotransferase may have an amino acid sequence of SEQ ID NO: 1, and the 2,4-diaminobutanoate decarboxylase may have an amino acid sequence of SEQ ID NO: 2.

In the present disclosure, the gene encoding the 2-ketoglutarate 4-aminotransferase may have a base sequence of SEQ ID NO: 3 or SEQ ID NO: 4, and the gene encoding the 2,4-diaminobutanoate decarboxylase may have a base sequence of SEQ ID NO: 5 or SEQ ID NO: 6.

In still another exemplary embodiment of the present disclosure, in order to improve production capacity of the 1,3-diaminopropane by over-expressing the ppc or the aspC, a recombinant plasmid p15DD$^{opt}$ppc was constructed by inserting the ppc in the p15DD$^{opt}$, and then, p15DD$^{opt}$paspC was constructed by positioning the aspC gene behind the tac promoter in the p15DD$^{opt}$.

In the present disclosure, the gene encoding the 2-ketoglutarate 4-aminotransferase (dat) and the gene encoding 2,4-diaminobutanoate decarboxylase (ddc) are introduced in the recombinant microorganism in a form in which the genes are inserted in one vector, but the present disclosure is not limited thereto. Specifically, any one or both of the genes encoding the enzyme involved in the metabolic pathway of 1,3-diaminopropane may be directly introduced onto chromosome of the host microorganism, and may be introduced into the host microorganism in a form of a recombinant vector produced by inserting any one or both of the genes in an expression vector.

In the present disclosure, the strong promoter contained in the vector may be selected from the group consisting of a trc promoter, a tac promoter, a T7 promoter, a lac promoter, and a trp promoter, and specifically, the tac promoter is preferred. However, the strong promoter is not limited thereto.

In the present disclosure, the vector means a DNA construct including DNA sequences operably linked to an appropriate control sequence capable of expressing DNA in an appropriate host. The vector may be a plasmid, phage particles, or simply be a potential genomic insert. When the vector is transformed into the appropriate host, the vector may replicate and function regardless of the host genome, or in some cases, may be incorporated with the genome itself. The plasmid is the most generally used form of the vector at present, such that the plasmid and the vector used herein are sometimes interchangeably used. In view of a purpose of the present disclosure, it is preferable to use a plasmid vector. A typical plasmid vector which is usable for the purpose has a structure including (a) a replication origin for effective replication so as to include hundreds of plasmid vectors per a host cell, (b) an antibiotic resistance gene capable of selecting the host cell transformed with the plasmid vector, and (c) a restriction enzyme cleavage site at which a foreign DNA fragment is able to be inserted. Even though the appropriate restriction enzyme cleavage site does not exist, ligation between the vector and the foreign DNA may be easily obtained by using a synthetic oligonucleotide adaptor or a linker according to general methods.

After the ligation, the vector is required to be transformed into the appropriate host cell. The transformation may be easily achieved by using a calcium chloride method described in document (Sambrook, et al., supra, Section 1.82). Alternatively, electroporation (Neumann, et al., *EMBO J.*, 1:841, 1982) may also be used for transformation of these cells.

As known in the art, in order to increase the expression level of the transfected gene in the host cell, the corresponding gene needs to be operably linked to transcriptional and translational expression control sequences that exert function in the selected expression host. Preferably, the expression control sequence and the corresponding gene are included in one recombinant vector including a bacterial selectable marker and a replication origin together.

The host cell transformed by the above-described recombinant vector forms a still another aspect of the present disclosure. The term 'transformation' used herein means that DNA is replicable as a chromosomal extrinsic factor or by chromosomal integration completion by introducing DNA into the host. A method for transformation includes any method in which nucleic acids are introduced into an organism, a cell, a tissue, or an organ, and may be performed by selecting an appropriate standard technology depending on the host cell as known in the art. The method for transformation includes electroporation, protoplast fusion, calcium phosphate ($CaPO_4$) precipitation, calcium chloride ($CaCl_2$) precipitation, stirring with silicon carbide fibers, *agrobacterium*-mediated transformation, PEG, dextran sulfate, lipofectamine and dryness/inhibition-mediated transformation; however, the present disclosure is not limited thereto. The host cell of the present disclosure may be a prokaryotic cell or a eukaryotic cell. In addition, a host in which an introduction efficiency of DNA is high, and an expression efficiency of the introduced DNA is high is generally used. Cells of known eukaryotic and prokaryotic hosts such as *escherichia coli, pseudomonas, bacillus, streptomyces*, fungi, and yeast, insect cells such as *Spodoptera frugiperda* (SF9), animal cells such as CHO and mouse cells, African green monkey cells such as COS 1, COS 7, BSC 1, BSC 40, and BMT 10, and tissue-cultured human cells are examples of host cells to be usable.

It should be understood that all vectors do not equally exert function in expressing DNA sequences of the present disclosure. Similarly, all of the host cells do not exert the function equally to the same expression system. However, those skilled in the art are able to have an appropriate selection among various vectors, expression control sequences, and hosts without departing from the scope of the present disclosure without undue experimental burden. For example, the host needs to be considered in selecting the vector, which is because the host is required to replicate in the host. Replication numbers of the vector, ability to control the replication numbers, and other proteins encoded by the vector, for example, expression of an antibiotic marker are also required to be considered. In selecting the expression control sequence, a number of factors need to be considered. For example, relative strength of the sequence, control possibility, and compatibility with the DNA sequences of the present disclosure, etc., are required to be considered with respect to a possible secondary structure. A single cell host is required to be selected in consideration of factors such as the selected vector, toxicity of a product encoded by the DNA sequence of the present disclosure, secretion property, ability to precisely fold the protein, culture and fermentation requirements, easiness in purifying the product encoded by the DNA sequence of the present disclosure from the host, etc. Within the scope of these variables, those skilled in the art may select various combinations of vectors/expression control sequences/hosts capable of fermenting the DNA sequences of the present disclosure or expressing the DNA sequences in large scale animal culture. As a screening method when cloning cDNA of an NSP protein by expression cloning, a binding method, a panning method, a film emulsion method, etc., may be applied.

In still another exemplary embodiment of the present disclosure, it was confirmed that when culturing the recombinant microorganism into which dat (the gene encoding 2-ketoglutarate 4-aminotransferase) and ddc (the gene encoding 2,4-diaminobutanoate decarboxylase) were introduced, and the recombinant microorganism into which $dat^{opt}$ (the gene encoding 2-ketoglutarate 4-aminotransferase optimized in codon of the *E. coli*) and $ddc^{opt}$ (the gene encoding 2,4-diaminobutanoate decarboxylase optimized in codon of the *E. coli*) were introduced, 65 mg/L and 144 mg/L of 1,3-diaminopropane were produced, respectively. In addition, it was confirmed that when culturing the recombinant microorganism into which the dat and ddc were introduced and in which C of $1034^{th}$ base sequence of the gene encoding aspartokinase I is substituted with T, or C of $1055^{th}$ base sequence of the gene encoding aspartokinase III is substituted with T, and the recombinant microorganism into which the $dat^{opt}$ and $ddc^{opt}$ were introduced, 89 mg/L and 175 mg/L of 1,3-diaminopropane were produced, respectively. Further, it was confirmed that when culturing a recombinant microorganism in which a promoter of ppc (the gene encoding phosphoenolpyruvate carboxylase) was substituted with trc so as to increase a pool of oxaloacetate, and culturing a recombinant microorganism in which a promoter of aspC (the gene encoding aspartate aminotransferase) was substituted with trc so as to increase a pool of aspartate, in the above recombinant microorganism, 182 mg/L and 282 mg/L of 1,3-diaminopropane were produced, respectively. Further, it was confirmed that when culturing a recombinant microorganism in which pfkA (the gene encoding phosphofructokinase I) was deleted from the recombinant microorganism in which the promoter of ppc and the promoter of aspC were substituted with trc so as to increase a pool of NADPH, in the above recombinant microorganism, 680 mg/L of 1,3-diaminopropane were produced. In addition, it was confirmed that when culturing a recombinant microorganism in which the ppc was over-expressed on the vector, and a recombinant microorganism in which the aspC was over-expressed on the vector in order to increase the pool of the oxaloacetate or the pool of the aspartate, in the recombinant microorganism from which pfkA was deleted, 1391 mg/L and 1349 mg/L of 1,3-diaminopropane were produced, respectively.

In another aspect of the present disclosure, the present disclosure relates to a method for producing a recombinant microorganism producing 1,3-diaminopropane including introducing a gene encoding 2-ketoglutarate 4-aminotransferase (dat) and a gene encoding 2,4-diaminobutanoate decarboxylase (ddc) into a microorganism having an ability of producing aspartate-4-semialdehyde (ASA).

In still another aspect of the present disclosure, the present disclosure relates to a method for producing 1,3-diaminopropane including: (a) producing 1,3-diaminopropane by culturing the recombinant microorganism; and (b) recovering the produced 1,3-diaminopropane.

Hereinafter, the present disclosure is described in detail with reference to Examples. These Examples are only provided to specifically explain the present disclosure, and it will be obvious to those skilled in the art that the technical scope of the present disclosure is not construed to be limited to these Examples.

EXAMPLE 1

Construction of Vector Containing Gene Involved in the Production of 1,3-Diaminopropane 1-1: Construction of p15DD Vector Containing dat and ddc PCR was performed with DNA (SEQ ID NO: 3) of 2-ketoglutarate 4-aminotransferase (dat) derived from *Acinetobacter baumannii* ATCC 19606 strain as a template, and primers of SEQ ID NOs: 9 and 10. The DNA was heated for 2 minutes at 95° C., followed by denaturation for further 30 seconds. The DNA was combined with the primer for 40 seconds at 55° C., and polymerized for 50 seconds at 72° C. The process from the DNA denaturation to polymerization was repeated 30 times, and the obtained product was maintained for 10 minutes at 72° C., and then, the temperature was lowered to 4° C. to terminate the PCR.

Next, the dat fragment and a pTac15k plasmid (p15A origin, low copies, $Km^R$, KAISTMBEL labstock) performing strong gene expression with a tac promoter were treated with restriction enzymes (EcoRI and KpnI), and then, treated with T4 DNA ligase to bind the dat fragment and the pTac15k plasmid cut with the restriction enzymes, thereby constructing a recombinant plasmid p15D.

In addition, PCR was performed with DNA (SEQ ID NO: 5) of 2,4-diaminobutanoate decarboxylase (ddc) derived from *Acinetobacter baumannii* ATCC 19606 strain as a template, and primers of SEQ ID NOs: 11 and 12 under the same condition as described above, thereby producing a ddc gene fragment.

Next, the ddc gene fragment and the p15D plasmid were treated with restriction enzymes (KpnI and PstI), and then, treated with T4 DNA ligase to bind the ddc fragment and the p15D plasmid cut with the restriction enzymes, thereby constructing a recombinant plasmid p15DD (FIG. 2).

1-2: Construction of p15DD$^{opt}$ Vector Containing dat$^{opt}$ and ddc$^{opt}$ In order to increase expression in *E. coli* of 2-ketoglutarate 4-aminotransferase derived from the *Acinetobacter baumannii* ATCC 19606 strain, dat$^{opt}$ gene (SEQ ID NO: 4) optimized in codon of *E. coli* was synthesized by Bioneer Corporation (Daej eon, Korea), and was provided in a pGEM-B1-dat$^{opt}$ plasmid form. PCR was performed with dat$^{opt}$ gene in the pGEM-B1-dat$^{opt}$ plasmid as a template, and primers of SEQ ID NOs: 9 and 10 under the same condition as Example 1-1, thereby producing a dat$^{opt}$ gene fragment.

Next, the dat$^{opt}$ fragment and a pTac15k plasmid (p15A origin, low copies, $Km^R$, KAISTMBEL labstock) performing strong gene expression with a tac promoter were treated with restriction enzymes (EcoRI and KpnI), and treated with T4 DNA ligase to bind the dat$^{opt}$ fragment and the pTac15k plasmid cut with the restriction enzymes, thereby constructing a recombinant plasmid p15D$^{opt}$.

In addition, in order to increase expression in *E. coli* of 2,4-diaminobutanoate decarboxylase derived from the *Acinetobacter baumannii* ATCC 19606 strain, dde$^{opt}$ gene (SEQ ID NO: 6) optimized in codon of *E. coli* was synthesized by Bioneer Corporation (Daej eon, Korea), and was provided in a pGEM-B1-ddc$^{opt}$ plasmid form. PCR was performed with dde$^{opt}$ gene in the pGEM-B1-dde$^{opt}$ plasmid as a template, and primers of SEQ ID NOs: 11 and 12 under the same condition as Example 1-1, thereby producing a dde$^{opt}$ gene fragment.

Next, the dde$^{opt}$ gene fragment and the p15D$^{opt}$ plasmid were treated with restriction enzymes (KpnI and PstI), and then, treated with T4 DNA ligase to bind the dde$^{opt}$ fragment and the p15D$^{opt}$ plasmid cut with the restriction enzymes, thereby constructing a recombinant plasmid p15DD$^{opt}$ (FIG. 3).

1-3: Construction of p15DD$^{opt}$ppc Vector

In order to improve the production capacity of the 1,3-diaminopropane by increasing pool of oxaloacetate (OAA), PCR was performed with DNA (SEQ ID NO: 7) of the gene (ppc) encoding phosphoenolpyruvate carboxylase derived from *E. coli* W3110 and converting phosphoenolpyruvate (PEP) into OAA as a template, and primers of SEQ ID NOs: 13 and 14 under the same condition as Example 1-1, thereby producing a ppc gene fragment. Further, PCR was performed with the p15DD$^{opt}$ vector produced in Example 1-2 as a template, and primers of SEQ ID NOs: 15 and 16 under the same condition as Example 1-1, thereby producing a fragment of the 15DD$^{opt}$ plasmid.

Next, the ppc gene fragment was bound to the fragment of the p15DD$^{opt}$ plasmid by a Gibson assembly method (Gibson et al., *Nat. Methods* 6:343-341, 2009), thereby constructing a recombinant plasmid, p15DD$^{opt}$ppc (FIG. 4).

1-4: Construction of p15DD$^{opt}$paspC Vector

In order to improve the production capacity of the 1,3-diaminopropane by increasing pool of aspartate (L-ASP), PCR was performed with DNA (SEQ ID NO: 8) of the gene (aspC) encoding aspartate aminotransferase derived from *E. coli* W3110 and converting OAA into L-ASP as a template, and primers of SEQ ID NOs: 17 and 18 under the same condition as Example 1-1, thereby producing an aspC gene fragment. Further, PCR was performed with the p15DD$^{opt}$ vector produced in Example 1-2 as a template, and primers of SEQ ID NOs: 15 and 16 under the same condition as Example 1-1, thereby producing a fragment of the p15DD$^{opt}$ plasmid.

Next, the aspC gene fragment was bound to the fragment of the p15DD$^{opt}$ plasmid by the Gibson assembly method (Gibson et al., *Nat. Methods* 6:343-341, 2009), thereby constructing a recombinant plasmid, p15DD$^{opt}$aspC. Further, in order to increase expression of the aspC, a tac promoter fragment was amplified by performing PCR with pTac15k as a template and primers of SEQ ID NOs: 19 and 20 under the same condition as Example 1-1, and a fragment of p15DD$^{opt}$apsC plasmid was produced by performing PCR with the p15DD$^{opt}$aspC plasmid as a template and primers of SEQ ID NOs: 15 and 21 under the same condition as Example 1-1. Then, the tac promoter fragment was bound to the fragment of p15DD$^{opt}$apsC plasmid by the Gibson assembly method reported in the art, and p15DD$^{opt}$paspC was finally constructed (FIG. 5).

EXAMPLE 2

Construction of Recombinant Microorganism Containing Recombinant Plasmid and Production of 1,3-Diaminopropane Using the Same 2-1: Construction of WL3110/p15DD Strain A WL3110/p15DD strain was produced by introducing the p15DD vector produced in Example 1-1 into a WL3110 (W3110 ΔlacI) strain produced by the method known in Korean Patent Laid-Open Publication No. 10-2009-0018781. Then, the produced strain was inoculated into an LB plate medium containing 25 mg/L of kanamycin, and cultured for 16 hours at 37° C. to select the recombinant microorganism.

2-2: Construction of WL3110/p15DD$^{opt}$ Strain

A WL3110/p15DD$^{opt}$ strain was produced by introducing the p15DD$^{opt}$ vector produced in Example 1-2 into a WL3110 (W3110 ΔlacI) strain. Then, the produced strain was inoculated into an LB plate medium containing 25 mg/L of kanamycin, and cultured for 16 hours at 37° C. to select the recombinant microorganism.

2-3: Construction of TH02/p15DD Strain

A TH02/p15DD strain was produced by introducing the p15DD vector produced in Example 1-1 into a TH02 strain (W3110 ΔlacI thr$^{AC1034T}$lysC$^{C1055T}$) wherein the TH02 strain was obtained by mutating C of 1034$^{th}$ sequence of the gene encoding aspartokinase I with T and mutating C of 1055$^{th}$ sequence of the gene encoding aspartokinase III with T in the WL3110 strain (W3110 ΔlacI). Then, the produced strain was inoculated into an LB plate medium containing 25 mg/L of kanamycin, and cultured for 16 hours at 37° C. to select the recombinant microorganism 2-4: Construction of TH02/p15DD$^{opt}$ Strain A TH02/p15DD$^{opt}$ strain was produced by introducing the p15DD$^{opt}$ vector produced in Example 1-2 into the TH02 strain (W3110 ΔlacI thr$^{AC1034T}$lysC$^{C1055T}$) produced in Example 2-3. Then, the produced strain was inoculated into an LB plate medium containing 25 mg/L of kanamycin, and cultured for 16 hours at 37° C. to select the recombinant microorganism.

2-5: Construction of DP01/p15DD$^{opt}$ Strain

A DP01/p15DD$^{opt}$ strain was produced by introducing the p15DD$^{opt}$ vector produced in Example 1-2 into a DP01 strain (W3110 ΔlacI thr$^{AC1034T}$lysC$^{C1055T}$ Pppc::Ptrc), wherein the DP01 strain was obtained by substituting the promoter of ppc with trc in the TH02 strain (W3110 ΔlacI thr$^{AC1034T}$lysC$^{C1055T}$) of Example 2-3. Then, the produced strain was inoculated into an LB plate medium containing 25 mg/L of kanamycin, and cultured for 16 hours at 37° C. to select the recombinant microorganism.

2-6: Construction of DP02/p15DD$^{opt}$ Strain

A DP02/p15DD$^{opt}$ strain was produced by introducing the p15DD$^{opt}$ vector produced in Example 1-2 into a DP02 strain (W3110 ΔlacI thr$^{AC1034T}$lysC$^{C1055T}$ Pppc::Ptrc PaspC::Ptrc), wherein the DP02 strain was obtained by substituting the promoter of aspC with trc in the DP01 strain (W3110 ΔlacI thr$^{AC1034T}$lysC$^{C1055T}$ Pppc::Ptrc) of Example 2-5. Then, the produced strain was inoculated into an LB plate medium containing 25 mg/L of kanamycin, and cultured for 16 hours at 37° C. to select the recombinant microorganism.

2-7: Construction of DP09/p15DD$^{opt}$ Strain

A DP09/p15DD$^{opt}$ strain was produced by introducing the p15DD$^{opt}$ vector produced in Example 1-2 into a DP09 strain (W3110 ΔlacI thr$^{AC1034T}$lysC$^{C1055T}$ Pppc::Ptrc PaspC::Ptrc ΔpfkA), wherein the DP09 strain was obtained by deleting pfkA from the DP02 strain (W3110 ΔlacI thr$^{AC1034T}$lysC$^{C1055T}$ Pppc::Ptrc PaspC::Ptrc) of Example 2-6. Then, the produced strain was inoculated into an LB plate medium containing 25 mg/L of kanamycin, and cultured for 16 hours at 37° C. to select the recombinant microorganism.

2-8: Construction of DP09/p15DD$^{opt}$ Strain

A DP09/p15DD$^{opt}$ppc strain was produced by introducing the p15DD$^{opt}$ppc vector produced in Example 1-3 into the DP09 strain (W3110 ΔlacI thr$^{AC1034T}$lysC$^{C1055T}$ Pppc::Ptrc PaspC::Ptrc ΔpfkA) of Example 2-7. Then, the produced strain was inoculated into an LB plate medium containing 25 mg/L of kanamycin, and cultured for 16 hours at 37° C. to select the recombinant microorganism.

2-9: Construction of DP09/p15DD$^{opt}$paspC Strain

A DP09/p15DD$^{opt}$paspC strain was produced by introducing the p15DD$^{opt}$paspC vector produced in Example 1-4 into the DP09 strain (W3110 ΔlacI thr$^{AC1034T}$lysC$^{C1055T}$ Pppc::Ptrc PaspC::Ptrc ΔpfkA) of Example 2-7. Then, the produced strain was inoculated into an LB plate medium containing 25 mg/L of kanamycin, and cultured for 16 hours at 37° C. to select the recombinant microorganism.

2-10: Production of 1,3-Diaminopropane Using Recombinant Microorganism

In order to confirm the production capacity of 1,3-diaminopropane of the recombinant microorganism, the strains of Examples 2-1 to 2-9 and Control strains (WL3110 and WL3110/pTac15k) were inoculated into an LB medium (10 mL), and pre-cultured for 8 hours at 37° C. Then, the pre-cultured culture fluid (1.5 mL) was inoculated into a 350 mL flask containing R/2 medium (30 mL). The R/2 medium consisted of 10 g glucose, 2 g (NH$_4$)$_2$HPO$_4$, 6.75 g KH$_2$PO$_4$, 0.85 g citric acid, 0.8 g MgSO$_4$.7H$_2$O, 3 g (NH$_4$)$_2$SO$_4$, and 5 mL trace metal solution per 1 L distilled water, and the trace metal solution contained 5 M HCl: 10 g FeSO$_4$.7H$_2$O, 2.25 g ZnSO$_4$.7H$_2$O, 1 g CuSO$_4$.5H$_2$O, 0.5 g MnSO$_4$.5H$_2$O, 0.23 g Na$_2$B$_4$O$_7$.10H$_2$O, 2 g CaCl$_2$.2H$_2$O, and 0.1 g (NH$_4$)$_6$MO$_7$O$_{24}$ per 1 L. The culturing was conducted by a shaking incubator (jSR, Korea) operating at 200 rpm for 36 hours at 37° C. After the culturing, a culture fluid was subjected to centrifugation at 13,200 rpm for 10 minutes by using a centrifuge, and the supernatant was collected to measure concentration of 1,3-diaminopropane through high performance liquid chromatography (HPLC) analysis.

As a result, as shown in Table 1 below, it could be confirmed that respective recombinant microorganisms produced different concentrations of 1,3-aminopropane.

TABLE 1

| Strain | 1,3-Diaminopropane concentration (mg/L) |
|---|---|
| WL3110 | 0 |
| WL3110/pTac15k | 0 |
| WL3110/p15DD | 65 |
| WL3110/p15DD$^{opt}$ | 144 |
| TH02/p15DD | 89 |
| TH02/p15DD$^{opt}$ | 175 |
| DP01/p15DD$^{opt}$ | 182 |
| DP02/p15DD$^{opt}$ | 282 |
| DP09/p15DD$^{opt}$ | 680 |
| DP09/p15DD$^{opt}$ppc | 1391 |
| DP09/p15DD$^{opt}$paspC | 1349 |

When the recombinant microorganism producing the 1,3-diaminopropane according to the present disclosure is used, 1,3-diaminopropane may be mass-produced to be industrially useful in various fields such as pharmaceutical products, agricultural products, fibers for clothing, etc.

Although specific embodiments of the present disclosure are described in detail, it will be apparent to those skilled in the art that the specific description is merely desirable exemplary embodiment and should not be construed as limiting the scope of the present disclosure. Therefore, the substantial scope of the present disclosure is defined by the accompanying claims and equivalent thereof.

The invention claimed is:

1. A recombinant microorganism producing 1,3-diaminopropane in which a gene encoding 2-ketoglutarate 4-aminotransferase (dat) and a gene encoding 2,4-diaminobutanoate decarboxylase (ddc) are introduced into a microorganism having an ability of producing aspartate-4-semialdehyde (ASA), wherein the recombinant microorganism comprises further mutation of base sequence of a gene encoding aspartokinase I and/or a gene encoding aspartokinase III to remove feedback inhibiting production of 1,3-diaminopropane, wherein the mutation of base sequence of a gene encoding aspartokinase I is the substitution of C of 1034th base sequence with T, and the mutation of base sequence of a gene encoding aspartokinase III is the substitution of C of 1055th base sequence with T, wherein the recombinant microorganism producing the 1,3-diaminopropane comprises further variation selected from the group consisting of:
(i) over-expression of a gene encoding aspartate aminotransferase; and
(ii) deletion of a gene encoding 6-phosphofructokinase I.

2. The recombinant microorganism of claim 1, wherein the microorganism having an ability of producing aspartate-4-semialdehyde (ASA) is selected from the group consisting of *Escherichia* genus, *Bacillus* genus, *Corynebacterium* genus, *Pichia* genus, *Pseudomonas* genus and *Saccharomyces* genus.

3. The recombinant microorganism of claim 1, wherein the over-expression comprises (i) substitution of a promoter of a gene encoding phosphoenolpyruvate carboxylase and/or the gene encoding aspartate aminotransferase with a strong promoter or (ii) introduction of an expression vector having a gene encoding phosphoenolpyruvate carboxylase and/or the gene encoding aspartate aminotransferase, and the strong promoter.

4. The recombinant microorganism of claim 3, wherein the strong promoter is selected from the group consisting of a trc promoter, a tac promoter, a T7promoter, a lac promoter, and a trp promoter.

5. The recombinant microorganism of claim 1, wherein the gene encoding the 2-ketoglutarate 4-aminotransferase (dat) and the gene encoding 2,4-diaminobutanoate decarboxylase (ddc) are derived from *Acinetobacter baumannii*.

6. The recombinant microorganism of claim 1, wherein the 2-ketoglutarate 4-aminotransferase has the amino acid sequence of SEQ ID NO: 1.

7. The recombinant microorganism of claim 1, wherein the 2,4-diaminobutanoate decarboxylase has the amino acid sequence of SEQ ID NO: 2.

8. The recombinant microorganism of claim 1, wherein the gene encoding the 2-ketoglutarate 4-aminotransferase has the base sequence of SEQ ID NO: 3 or SEQ ID NO: 4.

9. The recombinant microorganism of claim 1, wherein the gene encoding the 2,4-diaminobutanoate decarboxylase has the base sequence of SEQ ID NO: 5 or SEQ ID NO: 6.

10. The recombinant microorganism of claim 1, wherein the gene encoding the 2-ketoglutarate 4-aminotransferase (dat) and the gene encoding 2,4-diaminobutanoate decarboxylase (ddc) are introduced in the recombinant microorganism in a form in which the genes are inserted in one vector.

11. The recombinant microorganism of claim 10, wherein the vector has a strong promoter.

12. The recombinant microorganism of claim 11, wherein the strong promoter is selected from the group consisting of a trc promoter, a tac promoter, a T7 promoter, a lac promoter, and a trp promoter.

13. A method for producing 1,3-diaminopropane comprising:
(a) producing 1,3-diaminopropane by culturing the recombinant microorganism of claim 1; and
(b) recovering the produced 1,3-diaminopropane.

* * * * *

UNITED STATES PATENT AND TRADEMARK OFFICE
CERTIFICATE OF CORRECTION

PATENT NO. : 9,932,596 B2
APPLICATION NO. : 15/299928
DATED : April 3, 2018
INVENTOR(S) : Sang Yup Lee et al.

It is certified that error appears in the above-identified patent and that said Letters Patent is hereby corrected as shown below:

On Page 2, under References Cited, Column 2, Line 17: "Qian, Z., et al. "Metabolic Engineering of *Escherichia coli* for the Production of Cadaverine: A Five Carbon Diamine", "Biotechnology and Bioengineering", Sep. 1, 2010 pp. 91-103, vol. 108.", the page reference "pp. 91-103" should be -- pp. 93-103 --.

On Page 2, under References Cited, Column 2, Line 20: "Sambrook, J., et al. "Protocol II: Fresh Competent *E. coli* Prepared Using Calcium Chloride", "Molecular Cloning: A Laboratory Manual: Second Edition", 1989, pp. 1.81-1.84, Publisher: Cold Spring Harbor Laboratory Press, Published in: US.", the page reference "pp. 1.81-1.84" should be -- pp. 1.82-1.84 --.

Column 8, Line 7: "Daej eon" should be -- Daejeon --.

Column 8, Line 24: "Daej eon" should be -- Daejeon --.

Signed and Sealed this
Fifteenth Day of May, 2018

Andrei Iancu
*Director of the United States Patent and Trademark Office*